US00PP15064P2

(12) United States Plant Patent
Gray

(10) Patent No.: US PP15,064 P2
(45) Date of Patent: Aug. 3, 2004

(54) MANDEVILLA PLANT NAMED 'PINK VELVET'

(50) Latin Name: *Mandevilla hybrid*
Varietal Denomination: Pink Velvet

(75) Inventor: John F. Gray, Hawthorne, FL (US)

(73) Assignee: Lake Area Nursery, Hawthorne, FL (US)

( * ) Notice: Subject to any disclaimer, the term of this patent is extended or adjusted under 35 U.S.C. 154(b) by 0 days.

(21) Appl. No.: 10/716,014

(22) Filed: Nov. 18, 2003

(51) Int. Cl.[7] ..... A01H 5/00
(52) U.S. Cl. ..... Plt./232
(58) Field of Search ..... Plt./232

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of Mandevilla plant named 'Pink Velvet', characterized by its upright vining growth habit; glossy, dark green-colored leaves; dark pink-colored flowers with imbricate petals with ruffled margins; and tolerance to low and high temperatures.

2 Drawing Sheets

Botanical classification/cultivar designation: *Mandevilla hybrid* cultivar Pink Velvet.

BACKGROUND OF THE INVENTION

The present Invention relates to a new and distinct cultivar of Mandevilla plant, botanically known as *Mandevilla hybrid,* and hereinafter referred to by the name 'Pink Velvet'.

The new cultivar is a product of a planned breeding program conducted by the Inventor in Hawthorne, Fla. The objective of the breeding program was to develop new Mandevilla cultivars with attractive flower form and coloration.

The new cultivar originated from a self-pollination of the *Mandevilla hybrid* cultivar Alice DuPont, not patented, in Hawthorne, Fla., in 1996. The new cultivar was discovered and selected by the Inventor as a flowering plant within the progeny from this self-pollination in a controlled environment in Hawthorne, Fla., in 2000. The new cultivar was selected on the basis of its flower form and flower coloration.

Asexual reproduction of the new cultivar by terminal cuttings taken in Hawthorne, Fla., since spring, 2000, has shown that the unique features of this new Mandevilla are stable and reproduced true to type in successive generations.

SUMMARY OF THE INVENTION

Plants of the cultivar Pink Velvet have not been observed under all possible environmental conditions. The phenotype may vary somewhat with variations in environment such as temperature and light intensity without, however, any variance in genotype.

The following traits have been repeatedly observed and are determined to be the unique characteristics of 'Pink Velvet'. These characteristics in combination distinguish 'Pink Velvet' as a new and distinct cultivar:

1. Upright vining growth habit.
2. Glossy, dark green-colored leaves.
3. Dark pink-colored flowers with imbricate petals with ruffled margins.
4. Tolerant to low and high temperatures.

Plants of the new Mandevilla are most similar to plants of the parent cultivar, 'Alice DuPont'. In side-by-side comparisons conducted in Hawthorne, Fla., plants of the new Mandevilla differed from plants of the cultivar Alice DuPont in the following characteristics:

1. Leaves of plants of the new Mandevilla were smaller, smoother and glossier than leaves of plants of the cultivar Alice DuPont.
2. Plants of the new Mandevilla had smaller flowers than plants of the cultivar Alice DuPont.
3. Flower petals of plants of the new Mandevilla were more overlapping than flower petals of plants of the cultivar Alice DuPont.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Mandevilla.

The photograph on the first sheet comprises a side perspective view of a typical plant of 'Pink Velvet'.

The photograph on the second sheet is a close-up view of typical flowers and leaves of 'Pink Velvet'.

DETAILED BOTANICAL DESCRIPTION

In the following description, color references are made to The Royal Horticultural Society Colour Chart, 1995 Edition, except where general terms of ordinary dictionary significance are used. Plants used for this description were about one year old and grown in one-gallon containers in an outdoor nursery in Dallas/Fort Worth, Tex. area during the summer. Day temperatures ranged from 27 to 35° C. and night temperatures ranged from 21 to 27° C.

Botanical classification: *Mandevilla hybrid* cultivar Pink Velvet.

Parentage: Self-pollination of *Mandevilla hybrid* cultivar Alice DuPont, not patented.

Propagation:

*Type cutting.*—Terminal cuttings.

*Time to initiate roots, summer.*—About 21 days at 27° C.

*Time to initiate roots, winter.*—About 30 days at 21° C.

*Time to develop roots, summer.*—About 60 days at 27 to 32° C.

*Time to develop roots, winter.*—About 67 days at 24° C.

*Root description.*—Numerous, thick, fibrous and freely branching.

Plant description:

*Form.*—Perennial evergreen flowering plant; twining vine; initially upright, then vining, requires support to maintain upright habit. Plants are typically pinched about three months after planting to enhance lateral branch development; potentially two lateral branches form at every node.

*Plant height* (*length*).—About one meter.

*Plant diameter.*—About 35 cm.

*Vigor.*—Moderately vigorous.

*Lateral branches.*—Length: About 95 cm. Diameter: About 4 mm. Internode length: About 10 cm. Shape: Round in cross-section. Aspect: Initially upright, then trailing, requires support. Strength: Flexible, moderately strong. Texture: Rough; very fine white pubescence. Color: Young stems: 144A. Mature stems: Close to 148A occasionally overlain with close to 165A.

*Foliage description.*—Leaves simple, opposite; generally symmetrical and long-persisting. Length: About 16.5 cm. Width: About 8.7 cm. Shape: Elongated oblong. Apex: Acute to mostly cuspidate. Base: Cordate. Margin: Entire. Texture: Rugose, leathery, durable; both surfaces, glabrous. Luster: Upper surface, glossy; lower surface, somewhat glossy. Venation pattern: Pinnate. Petiole length: About 1 cm. Petiole diameter: About 5 mm. Petiole texture, upper surface: Slightly pubescent. Petiole texture, lower surface: Glabrous. Color: Developing and fully expanded foliage, upper surface: More green than 147A. Developing and fully expanded foliage, lower surface: Close to 147B. Venation, upper surface: Lateral veins, close to 147A; midvein, close to 146B to 146C. Venation, lower surface: Lateral veins, close to 147B to 147C; midvein, close to 150D. Petiole, upper and lower surfaces: Close to 146A to 146B.

Flower description:

*Flower type and habit.*—Single slaverform flower; terminal or axillary; flowers face mostly outward. Flowers self-cleaning. Freely flowering, more than 30 flowers per plant develop during the flowering season.

*Natural flowering season.*—Spring until frost in the autumn; flowering continuous.

*Flower longevity on the plant.*—About one to two weeks.

*Fragrance.*—Very faint, sweet.

*Flowers.*—Appearance: Flared trumpet, corolla fused, five-parted; petals imbricate; flowers star-shaped; petal color iridescent. Diameter: About 8.7 cm. Depth (length): About 5.3 cm. Corolla tube length: About 3.6 cm. Throat diameter: About 1.7 cm. Tube diameter, base: About 3 mm.

*Flower buds* (*just before opening*).—Length: About 5.5 mm. Diameter: About 1.7 cm. Shape: Oblong. Color: Close to 62A overlain with 57A.

*Corolla.*—Arrangement/appearance: Single whorl of five petals, fused into flared trumpet; overlapping. Petal length: About 7.3 cm. Petal width: About 3 cm. Petal shape: Roughly spatulate. Petal apex: Acute with cuspidate tendencies. Petal margin: Entire; undulate, ruffled appearance. Petal texture: Smooth, velvety. Color: Petal, upper surface, when opening and fully opened: Closest to 57A; towards the margins, close to 57B. Petal, lower surface, when opening and fully opened: 57A to 57C. Tube, fully opened: 57A; towards the base, close to 155D overlain with 57A. Throat, fully opened: 57A; towards the base, close to 9A.

*Sepals.*—Arrangement/appearance: Five per flower in a single whorl; fused, campanulate; reflexed. Length: About 9 mm. Width: About 2.5 mm. Shape: Elongated, linear. Apex: Sharply acute. Margin: Entire. Texture: Smooth, slightly waxy. Color, upper and lower surfaces: 144B; towards apex, overlain with close to 53A.

*Peduncles.*—Length: About 1.5 cm. Diameter: About 3 mm. Angle: Bent. Strength: Flexible, but strong. Color: Initially 144A; with development, overlain with 46A to 53A.

*Reproductive organs.*—Stamens: Quantity: Five; filaments fused to corolla. Anther shape: Oblong, elongated. Anther size: About 5 mm by 2 mm. Anther color: 8C. Pollen: None observed. Pistils: Quantity: One. Pistil length: About 2.1 cm. Stigma shape: Rounded. Stigma color: Close to 155D. Style color: Close to 155D. Ovary color: Close to 144A to 144B.

*Seed/fruit.*—Seed and fruit production has not been observed.

Disease/pest resistance: Plants of the new Mandevilla have not been noted to be resistant to pathogens and pests common to Mandevilla.

Temperature tolerance: Plants of the new Mandevilla have been observed to be tolerant to rain and wind and tolerant to temperatures from zero to higher than 43° C.

It is claimed:

1. A new and distinct cultivar of Mandevilla plant named 'Pink Velvet', as illustrated and described.

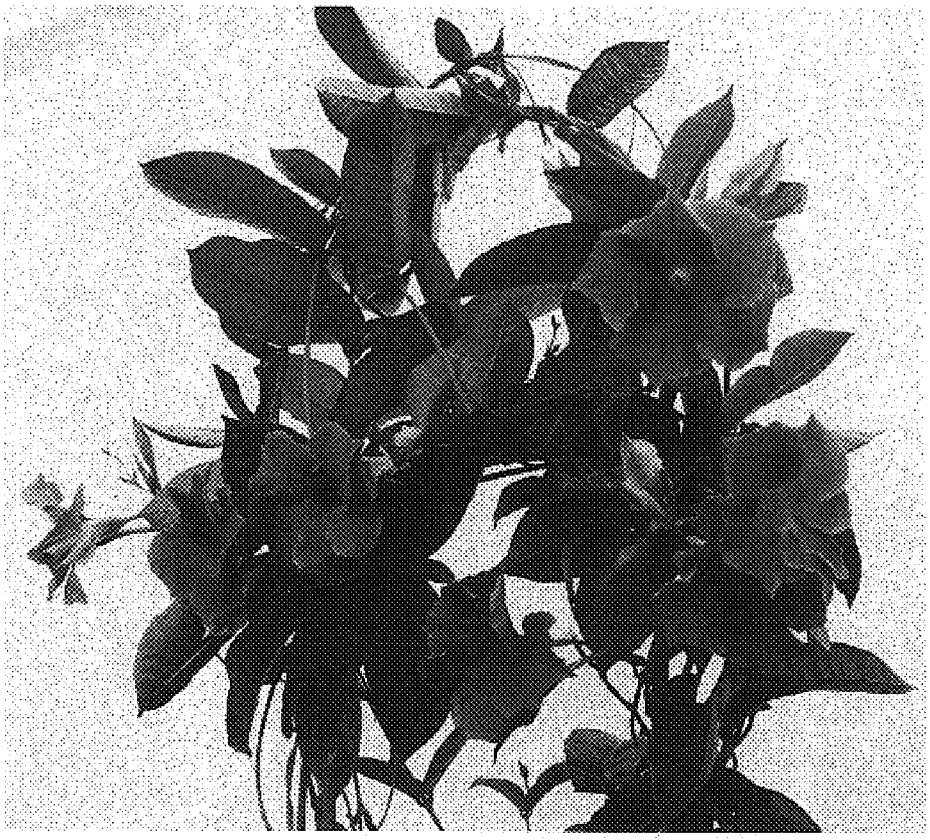

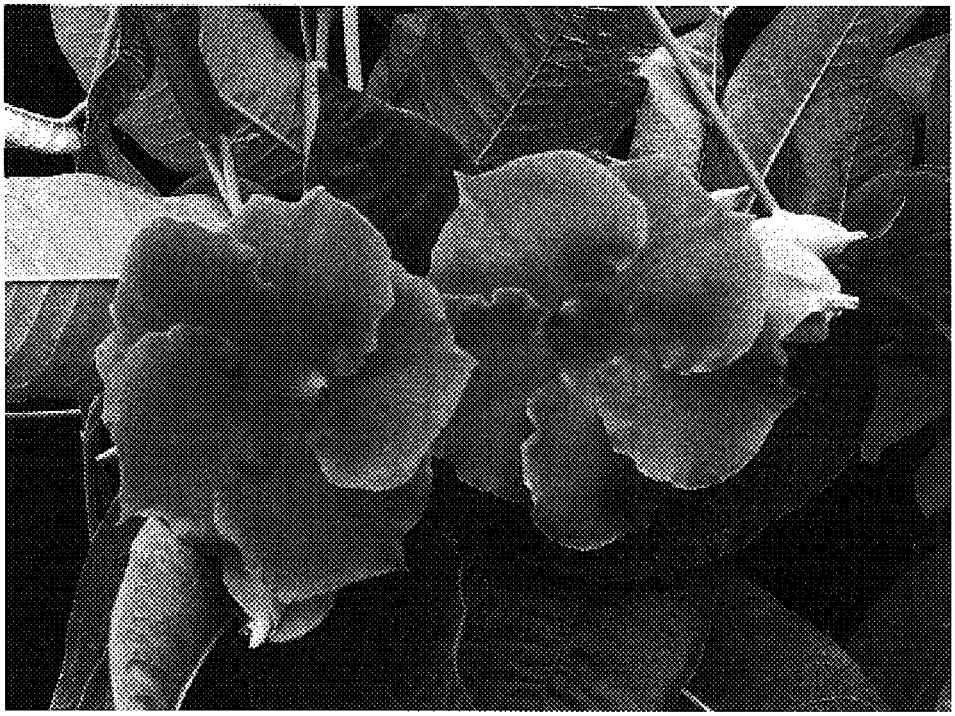

* * * * *